United States Patent [19]

Abe et al.

[11] Patent Number: 4,594,878
[45] Date of Patent: Jun. 17, 1986

[54] DYNAMIC FRICTION COEFFICIENT MEASURING APPARATUS

[75] Inventors: Yuya Abe, Tokyo; Toshio Sawa, Sayama, both of Japan

[73] Assignee: Nippo Sangyo Co. Ltd., Kokubunjii, Japan

[21] Appl. No.: 622,345

[22] Filed: Jun. 19, 1984

[30] Foreign Application Priority Data

Jun. 24, 1983 [JP] Japan ............................ 58-112658
Jan. 18, 1984 [JP] Japan ............................ 59-005652

[51] Int. Cl.[4] ............................................ G01N 19/02
[52] U.S. Cl. ............................................ 73/9; 73/146
[58] Field of Search ............................ 73/9, 146, 10

[56] References Cited

U.S. PATENT DOCUMENTS

| | | | |
|---|---|---|---|
| 2,990,713 | 7/1961 | Hellefinger et al. | 73/9 |
| 3,059,464 | 10/1962 | Deane | 73/9 |
| 3,152,468 | 10/1964 | Powell et al. | 73/146 X |
| 3,194,051 | 7/1965 | Schnoll | 73/9 |
| 3,717,025 | 2/1973 | Kronenberg et al. | 73/9 |
| 4,051,713 | 10/1977 | Bao et al. | 73/9 |
| 4,098,111 | 7/1978 | Hordmärk et al. | 73/9 |
| 4,425,785 | 1/1984 | Davis | 73/9 |
| 4,458,527 | 7/1984 | McFarland et al. | 73/9 X |

FOREIGN PATENT DOCUMENTS

| | | | |
|---|---|---|---|
| 349310 | 6/1937 | Italy | 73/9 |
| 2967 | 1/1980 | Japan | 73/9 |
| 57-23212 | 5/1982 | Japan | 73/9 |
| 157549 | 3/1963 | U.S.S.R. | 73/9 |
| 274431 | 9/1970 | U.S.S.R. | 73/9 |
| 369450 | 4/1973 | U.S.S.R. | 73/9 |
| 685938 | 9/1979 | U.S.S.R. | 73/9 |

OTHER PUBLICATIONS

"Bearing Dynamometer"; *The Review of Scientific Instruments;* vol. 30, No. 9, pp. 775-777; Sep. 1959; R. V. Klint et al.

"Electrical Automatic Measurement of Resistance of Rolling Wheel on Undulated Soft Ground"; *Oyo Buturi* (Japan); vol. 50, No. 2, pp. 137-144; Feb. 1981; Hisashi Ohta et al.

Primary Examiner—Stewart J. Levy
Assistant Examiner—Tom Noland
Attorney, Agent, or Firm—Beveridge, DeGrandi & Weilacher

[57] ABSTRACT

A dynamic friction coefficient measuring apparatus includes a friction measuring portion having a disc with a friction measuring rubber member attached thereto, a driving disc adapted to rotate coaxially with the disc and a dynamometer which interconnects the disc and the driving disc. A tachometer measures the speed of the rubber member during rotation of the friction measuring portion. An X-Y recorder records two electric outputs of the friction measuring portion and the tachometer onto rectangular coordinates.

11 Claims, 13 Drawing Figures

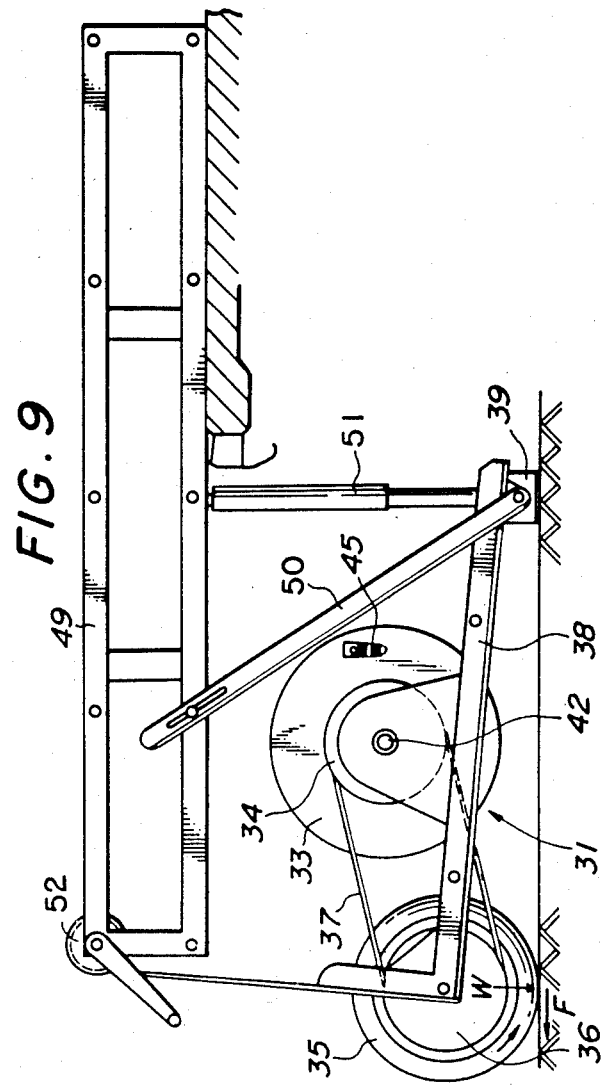

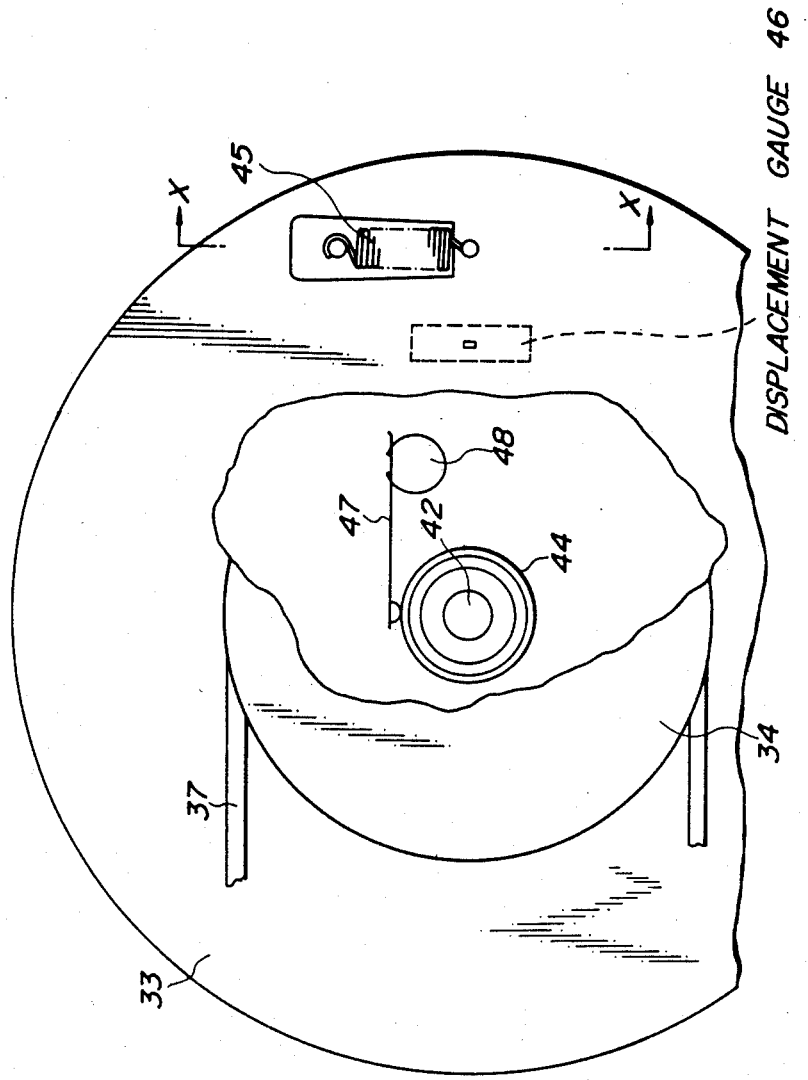

DYNAMIC FRICTION COEFFICIENT MEASURING APPARATUS

BACKGROUND OF THE INVENTION

The present invention relates to a dynamic friction coefficient measuring apparatus capable of continuously measuring and automatically recording dynamic friction forces between two different objects according to speeds.

For example, for measuring a dynamic friction force between a road surface and an automobile tire, there has heretofore been used a pendulum type measuring apparatus. However, this pendulum type measuring apparatus has been applicable to the measurement of friction only when the speed relative to the road surface is within a fairly low speed range. But, the friction coefficient of the road surface differs considerably according to running speeds of an automobile. Generally, the higher the speed, the smaller the friction coefficient. Besides, it is at a high speed of 40 km/H or more that such friction coefficient becomes a subject of question. Therefore, in order to measure the friction coefficient correctly, it is necessary that the speed be measured under the same condition as the actual speed and that the pressure be also measured under the same condition as the actual pressure of ground contact of a tire.

To satisfy such requirements, the present inventor has already proposed a friction coefficient measuring apparatus (see Japanese Patent Publication No. 57-23212) including a friction measuring portion, the friction measuring portion comprising a disc-like body with a road surface friction measuring rubber member attached thereto, a disc as a rotating body capable of rotating about the axis of the disc-like body, the disc-like body and the disc being interconnected through a first spring member, and a pen holder capable of moving in the radial direction of the disc, the pen holder being connected to the disc through a second spring member, in which the relation between the speed of the friction coefficient measuring rubber member and the amount of displacement in the radial direction of the pen holder during rotation of the friction measuring portion, and the relation between the angle of torsion of the disc relative to the disc-like body and the friction coefficient, are calibrated in advance to thereby record the relation between the friction coefficient and the speed automatically.

However, such friction coefficient measuring apparatus has encountered a limit in measurement accuracy due to a sliding friction in the radial direction of the pen holder and that between the pen and the recording paper. Besides, the pen holder moves during a preliminary rotation of the disc-like body and the disc, thus allowing unnecessary recording to be made and making it difficult to read data. Further, the operation for attaching and detaching the pen and that for fixing the recording paper are troublesome, and thus the working efficiency is poor.

Accordingly, it is the object of the present invention to provide a dynamic friction coefficient measuring apparatus capable of automatically recording the relation between speed and friction coefficient, attaining a high measurement accuracy and easily reading data and being easy to handle.

It is another object of the present invention to provide a dynamic friction coefficient measuring apparatus which, once set on a road surface, permits a continuous and automatic recording of the relation between speed and friction coefficient, attains a high measurement accuracy and an easy reading of data, and is easy to handle.

SUMMARY OF THE INVENTION

The apparatus of the present invention includes a friction measuring portion, the friction measuring portion having a disc with a friction measuring rubber member attached thereto, a driving disc adapted to rotate coaxially with the disc and a dynamometer which interconnects the disc and the driving disc; a tachometer for measuring the speed of the rubber member during rotation of the friction measuring portion, and an X-Y recorder for recording two electric outputs of the friction measuring portion and the tachometer onto rectangular coordinates. In such a construction, when the disc and the driving disc are rotated by means of a driving device such as a motor or the like and the rubber member attached to the disc is grounded to the surface of an object to be measured, the rotating speed of the disc lowers due to the action of a frictional force, and the resultant torsion between the disc and the driving disc is detected by the dynamometer to determine the frictional force, while at the same time the speed of the rubber member is measured by the tachometer, then these measured data are fed as electric outputs to the X-Y recorder, which records the speed and friction coefficient onto rectangular coordinates. Thus, since the measured values of frictional force and speed are taken out as electrical outputs, the measurement accuracy is improved, and since recording is made onto rectangular coordinates (by the X-Y recorder) and no unnecessary recording is made, it becomes easier to read data and the handling operation becomes simpler. And in the pendulum type measuring apparatus, the measurement of friction is limited to the case where the speed relative to the road surface is constant and the speed of the car is constant. However, the friction coefficient of a road surface differs considerably according to running speeds of a car, and generally the higher the speed, the smaller the friction coefficient. For the purpose of measuring friction coefficient at high speeds, the road surface friction measuring car has come to be used. But, this measuring car measures a friction coefficient through a genuine measuring tire while running at a predetermined measurement speed, so in order to measure friction coefficients of a certain road surface at various speeds, it is necessary for the car to run on the road surface repeatedly at different speeds, and thus the measurement on a busy street is difficult.

In order to achieve the above-mentioned object, there is provided according to the present invention a dynamic friction coefficient measuring apparatus including a friction measuring portion, the friction measuring portion having a disc for driving a friction measuring test tire through a transmission belt or the like, a driving wheel adapted to rotate coaxially with the disc and a dynamometer which interconnects the disc and the driving wheel; a tachometer for measuring the peripheral speed of the test tire; and an X-Y recorder for recording two electric outputs of the friction measuring portion and the tachometer onto rectangular coordinates.

In such a construction, when the driving wheel is rotated by a driving device such as a motor or the like, the disc which is connected to the driving wheel through the dynamometer is rotated, so that the tire connected to the disc through a transmission belt or the like is rotated. When this tire is contacted with the surface of an object to be measured, the rotating speed of the tire is decreased by the action of a frictional force, and the rotational speed of the disc interlocked with the tire also decreases. At this time, the frictional force of the tire is measured by the dynamometer which interconnects the disc and the driving wheel, and the pheripheral speed (speed relative to the surface of the object being measured) of the tire is measured by the tachometer. These measured data are fed as electric outputs to the X-Y recorder, whereby the speed and the friction coefficient are recorded onto rectangular coordinates. Thus, since the measured values of frictional force and speed are taken out as electric outputs, a high measurement accuracy can be attained, and since recording is made onto rectangular coordinates by the X-Y recorder, it becomes easier to read data. Further, since friction coefficients at all speeds from high speed to stop can be recorded in a single measurement, it becomes easier to effect measurement at actual places.

In practicing the present invention, the dynamometer is preferably composed of a spring balance which interconnects the disc and the driving wheel, and a displacement gauge for converting a displacement of the spring balance caused by torsion between the disc and the driving wheel into an electric quantity. Further, the tachometer preferably comprises an electric circuit in which, when the driving wheel and the tire are rotated preliminarily by means of a magnet motor and the motor is switched off to effect measurement, the motor is rotated interlockedly by the rotational force of the driving wheel, and at the same time the electromotive force included by the rotation of the magnet motor is measured.

In practicing the present invention, the dynamometer is preferably composed of a spring balance which interconnects the disc and the driving disc, and a displacement gauge for converting a displacement of the spring balance caused by torsion between the disc and the driving disc into an electric quantity.

Further, the tachometer preferably comprises an electric circuit in which, when the disc and the driving disc are rotated preliminarily by means of a magnet motor and then the motor is switched off to effect measurement, the motor is rotated interlockedly by the rotational force of the disc, and at this time the electromotive force induced by the rotation of the motor is measured.

BRIEF DESCRIPTION OF THE DRAWINGS

An embodiment of the present invention will be described hereinunder with reference to the drawings:

FIG. 8 is a plan view of another embodiment of the present invention;

FIG. 9 is a front view of the apparatus shown in FIG. 8;

FIG. 12 is a front view of the friction measuring portion shown in FIG. 11; and

DETAILED DESCRIPTION

Figure 1:
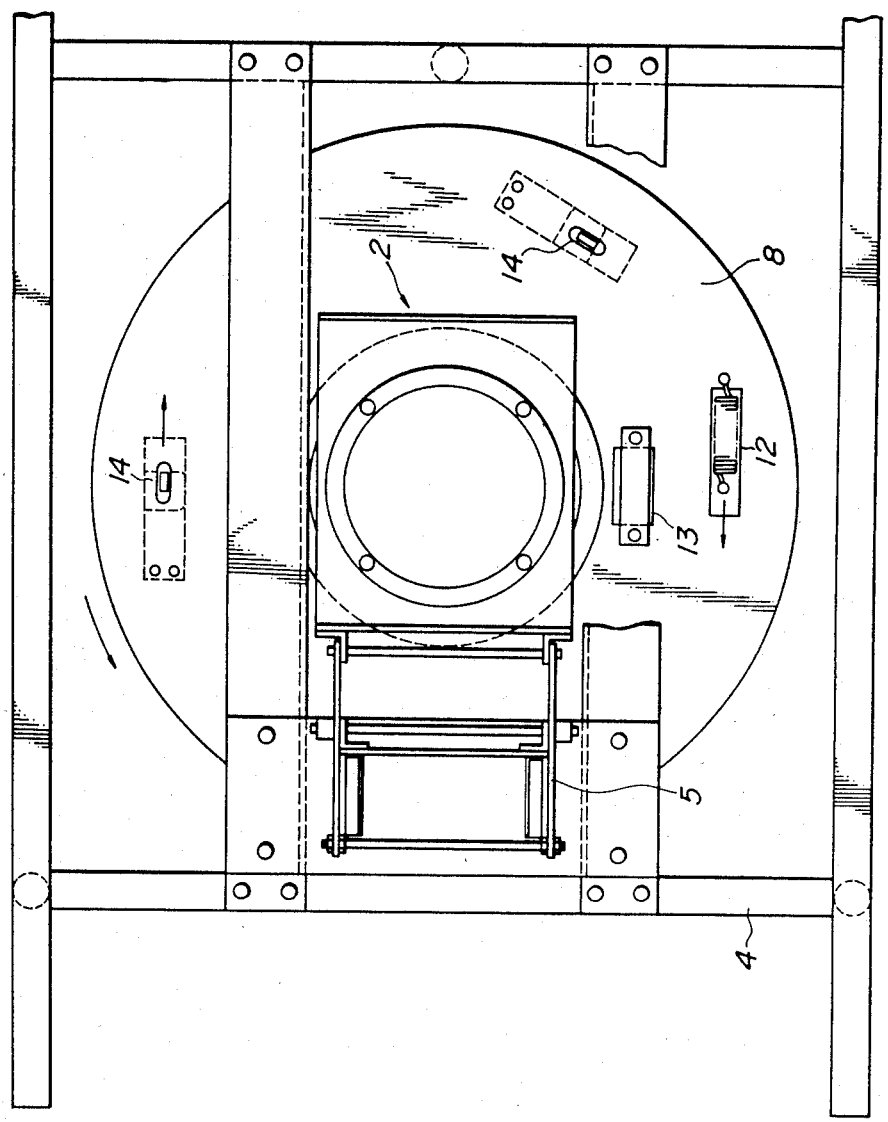
FIG. 1 is a plan view illustrating an embodiment of the present invention.
Figure 2:
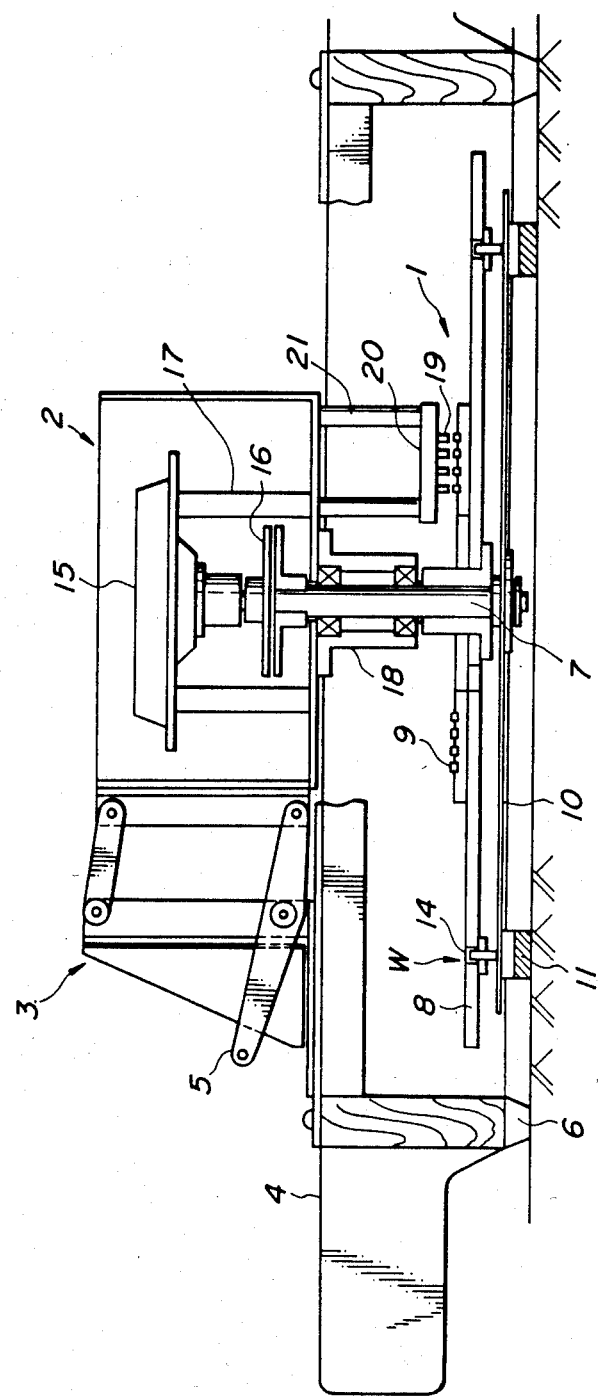
FIG. 2 is a front sectional view of the said embodiment.
Figure 3:
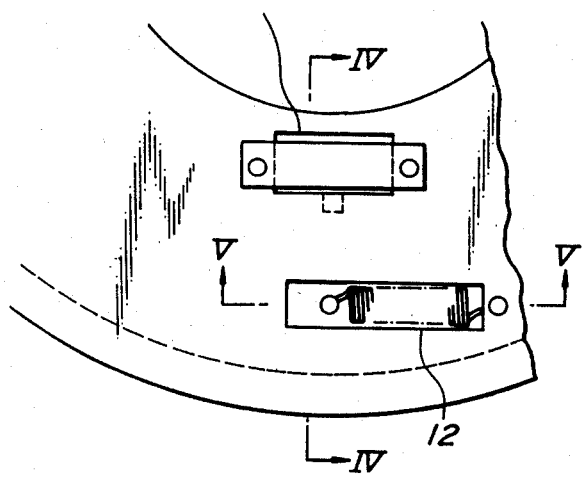
FIG. 3 is a partial plan view showing mounted states of a spring balance and a displacement gauge.
Figure 4:
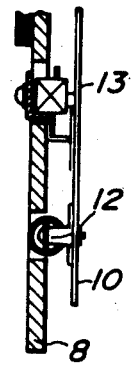
FIG. 4 is a sectional view taken along line IV—IV in FIG. 3.
Figure 5:
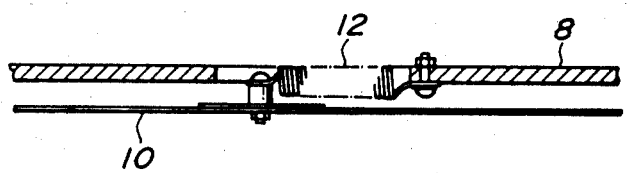
FIG. 5 is a sectional view taken along line V—V in FIG. 3.

As shown in FIGS. 1 and 2, the dynamic friction coefficient measuring apparatus of the present invention has a friction measuring portion 1 adapted to be rotated by a driving portion 2. The driving portion 2, which is supported by a holder 3 fixed onto a frame 4, is vertically movable together with the friction measuring portion 1 by moving a lever 5 up and down. A rubber seat 6 is attached to each of the four corners of the underside of the frame 4 for stably setting the entire apparatus onto the surface of an object to be measured, for example, a road surface. The friction measuring portion 1 has a driving disc 8 of a large inertia fixed to a driving shaft 7, with slip rings 9 being fixed onto the upper surface of the driving disc 8. Further, below the driving disc 8, a disc 10 of a small inertia is rotatably mounted on the driving shaft 7. To the lower surface of the disc 10 are fixed three friction coefficient measuring rubber members 11 concentrically with the driving shaft 7. Referring also to FIGS. 3 and 5, the driving disc 8 and the disc 10 are interconnected through a spring balance 12, thus allowing the disc 10 to rotate together with the driving disc 8 through the spring balance 12. Between the driving disc 8 and the disc 10 is mounted a displacement gauge 13 for measuring the amount of displacement of the spring balance 12 and converting it into an electric quantity when a load is imposed on the disc 10. Further, to the lower surface of the driving disc 8 is attached a roller 14 for applying a vertical load to the rubber members 11 fixed to the disc 10.

The driving portion 2 has a magnetic motor 15, whereby the driving shaft 7 is rotated through a coupler 16. The magnetic motor 15 is supported within a case of the driving portion 2 by motor supporting struts 17, and the driving shaft 7 is supported by a bearing 18 which is attached to the lower surface of the case of the driving portion 2. The driving portion 2 and the friction measuring portion 1 are adapted to move vertically integrally through the driving shaft 7.

During rotation of the friction measuring portion 1, electric outputs of the displacement gauge 13 are taken out from the slip rings 9 through brushes 19. The brushes 19 are attached to a brush holder 20 and fixed to the lower surface of the case of the driving portion 2 through supporting posts 21.

Figure 6:
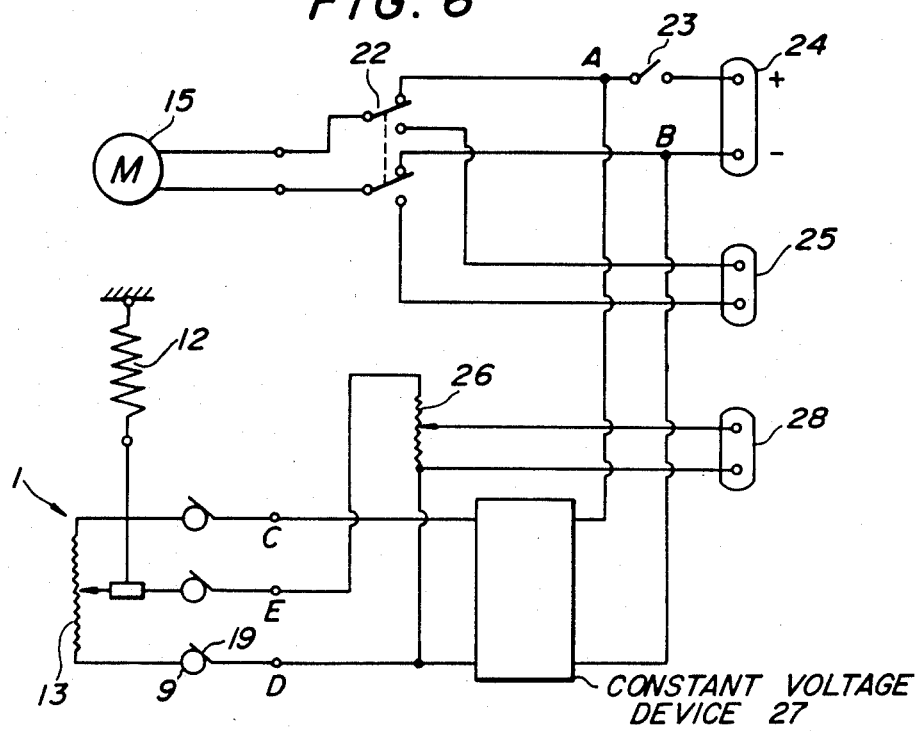
FIG. 6 is an electric circuit diagram of the said embodiment.
Figure 7:
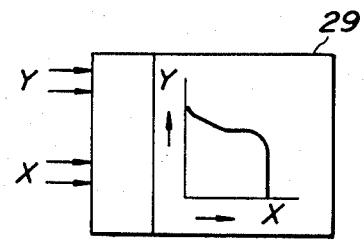
FIG. 7 is a view showing an X-Y recorder in the said embodiment.

In FIG. 6 there is illustrated an electric circuit of this dynamic friction coefficient measuring apparatus. The magnetic motor 15 is connected through a change-over switch 22 and a power switch 23 to a power terminal 24 which supplies DC voltage of, say, 12 V. Further, a speed output terminal 25 is connected to the change-over switch 22 and adapted to be connected to the magnetic motor 15 when the change-over switch 22 is switched from the state shown. To the power supply lines of the power terminal 24 is connected a constant voltage device 27 through contacts A and B, the constant voltage device 27 being connected also to input terminals C and D of the friction measuring portion 1. Further, output terminals E and D of the friction measuring portion 1 are connected to a friction coefficient output terminal 28 through an attenuator 26. The displacement gauge 13 receives a constant voltage from the constant voltage device 27 through input terminals C and D, brushes 19 and slip rings 9, and transmits an output voltage proportional to the amount of displacement of the spring balance 12 to the friction coefficient output terminal 28 through slip rings 9, brushes 19, output terminals E and D and attenuator 26. The attenuator 26 is preadjusted so as to provide a "1" output when a vertical load W imposed on the rubber member 11 and a frictional force F are equal to each other. Consequently, the output applied to the friction coefficient output terminal 28 represents friction coefficient $\mu$ in the friction coefficient formula $\mu = F/W$ ($\mu$ being friction coefficient). In this case, since the vertical load W is the weight of the friction measuring portion 1 plus the weight of the driving portion 2 and thus constant, it is sufficient for the attenuator 26 to be adjusted once. Further, as shown in FIG. 7, the speed output terminal 25 is connected to, for example, the X terminal of an X-Y recorder 29, and the friction coefficient output terminal 28 is connected to, for example, the Y terminal of the X-Y recorder 29.

In the construction described above, the measuring operation is performed in the following manner. First, the apparatus is placed on the surface of an object to be measured, for example, a road surface. In this state, the lever 5 is brought down to float the friction measuring portion 1 and the driving portion 2 above the road surface. Then, the change-over switch 22 is switched to the state shown in FIG. 6 and the power switch 23 is turned on, so that an electric current flows from the power terminal 24 to the magnetic motor 15, thus allowing the driving shaft 7 and hence the friction measuring portion 1 to rotate. When the rotating speed becomes higher than the measurement speed, the change-over switch 22 is turned to the opposite side from the state shown in FIG. 6 and at the same time the lever 5 is released slowly. Once the rubber members 11 contact the road surface, the action of a frictional force tries to stop the disc 10, but the driving disc 8 tries to continue rotating by virtue of inertia, so that there occurs torsion between the driving disc 8 and the disc 10. This torsional force causes displacement of the spring balance 12, and the amount of this displacement is measured by the displacement gauge 13. More specifically, the voltage from the power terminal 24 is fed to the displacement gauge 13 through the constant voltage device 27, and an output voltage proportional to the displacement of the spring balance 12 is applied from the displacement gauge 13 to the friction coefficient output terminal 28 through the attenuator 26. Consequently, this output is recorded as Y component of the X-Y recorder. On the other hand, the frictional force aplied to the rubber members 11 is transmitted to the driving disc 8 through the spring balance 12, so that the driving disc 8 is gradually decelerated and finally stops. During this period, the motor 15 rotates through and together with the driving shaft 7, so that it generates an electromotive force, which is applied to the speed output terminal 25 and recorded as X component of the X-Y recorder 29. In this case, the higher the rotating speed of the driving shaft 7, the larger the electromotive force of the motor 15, and therefore the X component represents speed. In this way, the relation between speed and friction coefficient is recorded on the rectangular coordinates of the X-Y recorder, so it is possible to know friction coefficients at various speeds in a single measuring operation.

Figure 11:
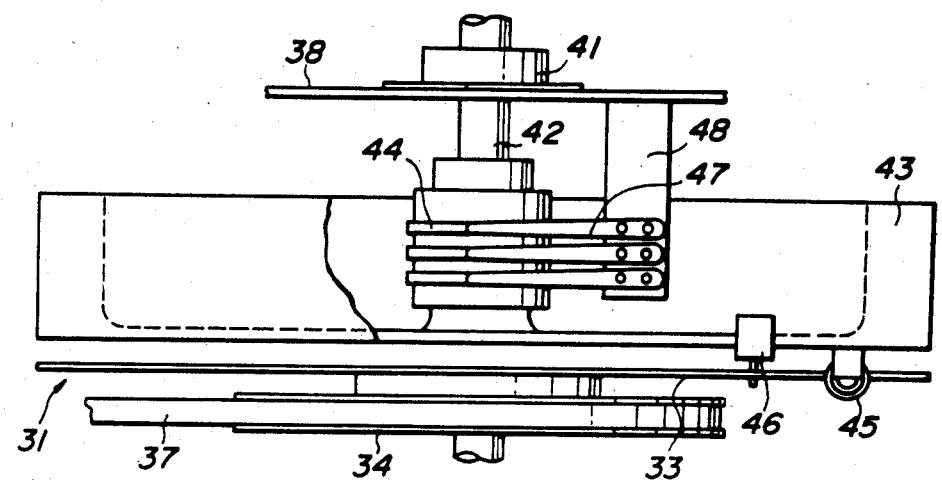
FIG. 11 is a plan view illustrating the details of a friction measuring portion in the embodiment shown in FIG. 8.
Figure 10:
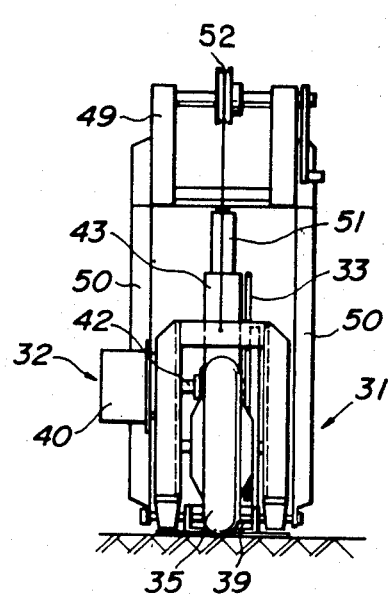
FIG. 10 is a side view of the apparatus shown in FIG. 8.
Figure 13:
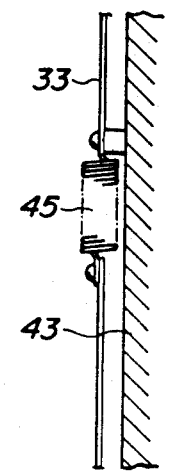
FIG. 13 is a sectional view taken along line X—X in FIG. 12.

FIGS. 8 to 12 show another embodiment of the present invention. In FIGS. 8 to 10, the dynamic friction coefficient measuring apparatus has a friction measuring portion which as a whole is indicated at 31 and adapted to be rotated by a driving portion indicated as a whole at 32. The rotation of the friction measuring portion 31 is transitted to a small-sized genuine tire 35 through a timing belt 37 which interconnects a pulley 34 fixed to a disc 33 and a pulley 36 fixed to the tire 35. The friction measuring portion 31, the driving portion 32 and the tire 35 are attached to a single frame 38. One end of the frame 38 is supported by a frame support 39 so as to be rotatable about the axis of the latter. The rotation of a magnetic motor 40 of the driving portion 32 is transmitted to a driving shaft 42 which is supported by bearing 41 mounted on both sides of the frame 38. The friction measuring portion 31 has a driving wheel 43 of a large inertia fixed to the driving shaft 42, and the disc 33 of a small inertia is rotatably mounted on the driving shaft 42 coaxially and in parallel with the driving wheel 43. Referring also to FIGS. 11 to 13, slip rings 44 are fixed to the boss of the driving wheel 43. The driving wheel 43 and the disc 33 are interconnected through a spring balance 45, and therefore the disc 33 is adapted to rotate together with the driving wheel 43 through the spring balance 45. Further, between the driving wheel 43 and the disc 33 is mounted a displacement gauge 46 for measuring the amount of displacement of the spring balance 45 and converting it into an electric amount. During rotation of the friction measuring portion 31, electric outputs of the displacement meter 46 are taken out from the slip rings 44 through brushes 47. The brushes 47 are attached to a brush holder 48 which is fixed to the frame 38. The frame support 39 which supports one end of the frame 38 is fixed to a road surface strongly under pressure by means of a supporting rod 50 and a jack 51 (FIG. 10), which are attached to a frame 49 mounted on a rear deck of a light van or the like. To the frame 49 is mounted a hoist 52 for floating the tire from the road surface during a preliminary rotation of the driving wheel 43 and the tire 35.

In this embodiment, an electric circuit, such as shown in FIG. 6 will be used.

The measuring operation in the above-described construction will now be explained. First, the apparatus is placed on the surface of an object to be measured, for example, a road surface, and the frame support 39 is fixed to the road surface strongly under pressure by the jack 51. Then, the tire 35 is floated by about 2 cm from the road surface by the hoist 52. In this state, the change-over switch 22 is switched to the state shown in FIG. 6 and the power switch 23 is turned on, so that an electric current flows from the power terminal 24 to the magnetic motor 15, thus allowing the driving shaft 32 to rotate. Consequently, the friction measuring portion 31 and the tire 35 connected thereto through the timing belt 37 are rotated. When the rotational speed becomes higher than the measurement speed, the change-over switch 22 is turned to the opposite side from the state shown in FIG. 6, and at the same time the tension of the hoist 52 is relieved slowly. Once the tire contacts the road surface, the action of a frictional force tries to stop the tire 35, but the driving wheel 43 which is rotating interlockedly with the tire 35 tries to continue rotating by virtue of inertia, so that there occurs torsion between the driving wheel 43 and the disc 33. This torsional force causes displacement of the spring balance 45, and the amount of this displacement is measured by the displacement gauge 46. More specifically, the voltage from the power terminal 24 is fed to the displacement gauge 43 through the constant voltage device 27, and an output voltage proportional to the displacement of the spring balance 45 is applied from the displacement gauge 46 to the friction coefficient output terminal 28 through the attenuator 26. Consequently, this output is recorded as Y component of the X-Y recorder 29 (see FIG. 7). On the other hand, the frictional force applied to the tire 35 is transmitted to the driving wheel 43 through the spring balance 45, so that the driving wheel 43 is gradually decelerated and finally stops. During whis period, the magnetic motor 15 rotates through and together with the driving shaft 42, so acts as a generator and produces an electromotive force proportional to the rotational speed. This electromotive force is applied to the speed output terminal 25 and recorded as X component of the X-Y recorder 29. In this way, the relation between speed and friction coefficient is recorded on the rectangular coordinates of the X-Y recorder, so it is possible to know friction coefficients at various speeds in a single measuring operation.

The dynamic friction coefficient measuring apparatus of the present invention is applicable not only to the measurement of friction coefficient between a road surface and a tire but also to other measurements, for example, the measurement of friction coefficient between shoes and a floor. In this case, it goes without saying that the rubber members 11 should be changed according to the material of the object to be measured.

According to the present invention, as set forth hereinabove, since friction coefficient and speed are converted to electric amounts and recorded automatically by the X-Y recorder, the measurement accuracy is improved, the measuring operation becomes easier, and the measurement is not affected by the measurer. Moreover, it is easy to read speed and friction coefficient because these are indicated on rectangular coordinates. Further, since the apparatus as a whole can be designed compactly, it is easy to carry and is therefore practical.

And also, according to the present invention, using a genuine tire, friction coefficients at various speeds from high speed to stop can be measured in a stationary condition on the road surface being measured. Besides, since friction coefficient and speed are converted to electric amount and recorded automatically by the X-Y recorder, the measurement accuracy is high, the measuring operation is easy, and the apparatus is easy to carry. Thus, outstanding practical effects are attained.

What is claimed is:

1. A dynamic friction coefficient measuring apparatus for continuously measuring and automatically recording dynamic frictional forces comprising:
   (A) a frame;
   (B) a driving means, including a permanent-magnet DC motor, for imparting a driving force in an activated mode and generating an electromotive force in a deactivated mode, said electromotive force being representative of speed of the motor in said deactivated mode;
   (C) a holder on said frame for supporting said driving means;
   (D) friction measuring means on said frame including
      a first disc having friction measuring rubber members disposed thereon,
      a driving disc connected to the motor for receiving the driving force and adapted to rotate coaxially with said first disc,
      dynamometer means responsive to coaxial displacement between said first disc and said driving disc for generating a first electrical signal indicative of said displacement,
   (E) tachometer means for receiving said electromotive force generated by the motor in said deactivated mode and for deriving a second electrical signal indicative of peripheral speed of said rubber members; and
   (F) an X-Y recorder for simultaneously recording said first and said second signals onto rectangular coordinates.

2. An apparatus as claimed in claim 1 wherein said dynamometer means includes a spring balance and a displacement gauge, said displacement gauge measuring the amount of displacement of the spring balance and generating said first signal in response thereto.

3. An apparatus as claimed in claim 1 wherein said first disc drives a friction measuring test tire through transmission means.

4. An apparatus as claimed in claim 3 wherein said dynamometer means includes a spring balance and a displacement gauge, said displacement gauge measuring the amount of displacement of the spring balance and generating said first signal in response thereto.

5. A method of measuring a dynamic coefficient of friction comprising:
   providing a permanent-magnet DC motor to set a friction measuring surface, connected to the motor, in motion at a predetermined speed;
   deactivating the motor to permit free motion of said friction measuring surface at a measuring speed;
   bringing said moving surface into contact with a test surface;
   generating by means of the motor an electromotive force indicative of the speed of said moving surface as said surface slows to a standstill;
   simultaneously recording said speed and torque on said surface as said surface comes to a standstill.

6. The method as claimed in claim 5 wherein said predetermined speed exceeds the measuring speed.

7. The method as claimed in claim 6 further comprising the steps of providing a changeover switch for controlling the motor, and two coaxial discs having a spring balance and a displacement measuring gauge for measuring said torque therebetween, wherein once said predetermined speed is attained, said changeover switch deactivates the motor to provide said electromotive force indicative of the instantaneous speed of said friction measuring surface, and said spring and gauge provide electromotive force indicative of torsional forces between said discs.

8. A dynamic friction coefficient measuring apparatus for continuously measuring and automatically recording dynamic frictional force between friction generating members and the surface of an object as a function of speed, said apparatus comprising:
   (A) frame means for supporting the apparatus over the surface of the object;

(B) friction measuring means on said frame comprising
- (i) first disc means adapted to be positioned over the surface of the object, said first disc means having friction generating members secured thereto,
- (ii) second disc means adapted to rotate coaxially with said first disc and in angular alignment or angular displacement with respect to said first disc,
- (iii) gauge means between said first disc and said second disc for detecting angular displacement between said discs while said discs are rotating, and
- (iv) means for converting said angular displacement to a first electrical signal indicative of friction force between said members and said surface when said members are sliding over said surface;

(C) means for driving said second disc means, said driving means comprising a permanent-magnet DC motor means for rotating said second disc in an electrically energized mode and for generating an electromotive force in an electrically deenergized mode, said electromotive force being representative of speed of the motor in said electrically deenergized mode.

(D) means for electrically energizing and deenergizing said motor means;

(E) means for raising and lowering said first disc over said surface, whereby said friction generating members can make sliding contact with said surface to thereby slow rotation of said first disc and said second disc;

(F) means for receiving said electromotive force generated by said motor in the electrically deenergized mode and for converting said electromotive force to a second electrical signal indicative of peripheral speed of said friction generating members; and (G) X-Y recorder means for simultaneously recording said first and said second signals onto rectangular coordinates to thereby display friction as a function of speed.

9. An apparatus as claimed in claim 8 wherein said means for detecting displacement includes a spring balance and a displacement gauge for measuring the amount of displacement of the spring balance and for generating said first signal in response thereto.

10. An apparatus as claimed in claim 8 wherein said first disc drives a friction measuring test tire through transmission means.

11. An apparatus as claimed in claim 10 wherein said means for detecting displacement includes a spring balance and a displacement gauge for measuring the amount of displacement of the spring balance and for generating said first signal in response thereto.

* * * * *